(12) United States Patent
Kajiya et al.

(10) Patent No.: US 11,311,585 B2
(45) Date of Patent: Apr. 26, 2022

(54) VE-CADHERIN EXPRESSION PROMOTING AGENT AND/OR INTEGRIN α5 EXPRESSION PROMOTING AGENT

(71) Applicant: Shiseido Company, Ltd., Tokyo (JP)

(72) Inventors: Kentaro Kajiya, Kanagawa (JP); Yuuko Matsumoto, Kanagawa (JP)

(73) Assignee: Shiseido Company, Ltd., Tokyo (JP)

( * ) Notice: Subject to any disclaimer, the term of this patent is extended or adjusted under 35 U.S.C. 154(b) by 74 days.

(21) Appl. No.: 16/764,573

(22) PCT Filed: Nov. 15, 2018

(86) PCT No.: PCT/JP2018/042363
§ 371 (c)(1),
(2) Date: May 15, 2020

(87) PCT Pub. No.: WO2019/098302
PCT Pub. Date: May 23, 2019

(65) Prior Publication Data
US 2021/0077556 A1 Mar. 18, 2021

(30) Foreign Application Priority Data
Nov. 17, 2017 (JP) .............................. JP2017-222117

(51) Int. Cl.
| *A61K 36/06* | (2006.01) |
| *A61K 36/254* | (2006.01) |
| *A61K 36/28* | (2006.01) |
| *A61K 36/64* | (2006.01) |

(52) U.S. Cl.
CPC ............ *A61K 36/06* (2013.01); *A61K 36/254* (2013.01); *A61K 36/28* (2013.01); *A61K 36/64* (2013.01)

(58) Field of Classification Search
CPC .......... A23V 2250/212; A23V 2300/10; A23V 2300/46; A23V 2002/00; A23V 2250/2124; A23L 5/30; A23L 19/10; A23L 5/13; A23L 5/17; A61K 36/258; A61K 36/06; A61K 36/062; A61K 36/254; A61K 36/28; A61K 36/64; A61K 36/064; A61K 8/9728; A61P 9/00; A61P 17/00; A61P 43/00; A61Q 19/00; A61Q 7/00
See application file for complete search history.

(56) References Cited

U.S. PATENT DOCUMENTS

| 5,676,956 A | 10/1997 | Duffy et al. |
| 8,367,124 B2 * | 2/2013 | Kajiya .................. A61P 17/16 424/725 |
| 2002/0155126 A1 | 10/2002 | Shirasu et al. |
| 2003/0162735 A1 | 8/2003 | Tkachuk |
| 2007/0134265 A1 | 6/2007 | Takada et al. |
| 2014/0127257 A1 | 5/2014 | Schiemann et al. |
| 2018/0264057 A1 | 9/2018 | Michalow et al. |

FOREIGN PATENT DOCUMENTS

| EP | 2 540 170 A1 | 1/2013 |
| JP | 63-277605 A | 11/1988 |
| JP | 2005-272413 A | 10/2005 |
| JP | 2011-201811 A1 | 10/2011 |
| KR | 10-2015-0126215 A | 11/2015 |
| KR | 10-2015-0126530 A | 11/2015 |
| KR | 10-2017-0114317 A | 10/2017 |
| WO | WO-2004/075621 A2 | 9/2004 |
| WO | WO-2017/183581 A1 | 10/2017 |

OTHER PUBLICATIONS

Shisheido Co, Ltd. "Shiseido Reveals the Relevance of Capillaries in Skin Elasticity" Pres Release, Oct. 2019, 2 pages. (Year: 2019).*
Avraamides et al., "Integrins in angiogenesis and lymphangiogenesis," Nat. Rev. Cancer, Aug. 2008, 8(8):604-617.
Iordache et al., "Effects of plant lectin and extracts on adhesion molecules of endothelial progenitors," Cent. Eur. J. Biol., 2011, 6(3):330-341.
Liu et al., "Integrin B1 is Required for Dermal Homeostasis," Journal of Investigative Dermatology, 2013 (online Nov. 29, 2012), 133:899-906.
Shiseido Group Press Release, "Discovery of Siberian ginseng acting on lymphatic vessels to improve 'swelling'," Shiseido Company, Limited, Jul. 5, 2016, two pages, with English translation two pages.
Parente et al., "Wound Healing and Anti-Inflammatory Effect in Animal Models of Calendula officinalis L. Growing in Brazil," Evidence-Based Complementary and Alternative Medicine, 2012, Article ID 375671, 1-7.

* cited by examiner

*Primary Examiner* — Aaron J Kosar
(74) *Attorney, Agent, or Firm* — Foley & Lardner LLP

(57) ABSTRACT

The purpose of the present invention is to provide a substance related to the stabilization of capillary blood vessels. This invention is based on the discovery that an extract from a plant selected from the group consisting of *Calendula officinalis*, Siberian ginseng, and *Cistanche salsa* increases gene expression of VE-cadherin or integrin α5.

4 Claims, 4 Drawing Sheets

(A)

(B)

(C)

(D)

VE-CADHERIN EXPRESSION PROMOTING AGENT AND/OR INTEGRIN α5 EXPRESSION PROMOTING AGENT

FIELD

The present invention relates to the technical field involved in the stabilization of capillaries.

BACKGROUND

Capillaries are fine blood vessels that connect arteries and veins, and play a role in supplying blood to the cells constituting the body. The blood supplied from capillaries can deliver oxygen and nutrients to the cells and collect carbon dioxide and waste products. It is known that the number of capillaries decreases with age and the decrease in the number of capillaries has an effect on the aging of various organs. For example, when the number of capillaries decrease, the activity of adenocytes decreases, then the secretion of mucus is reduced. Adenocytes exist in the skin, eyes, nose, mouth, throat, stomach, intestine, bladder, uterus, vagina, anus, etc. A decrease in the number of capillaries at these sites leads to a reduction in mucus secretion which, depending on the site, can be the cause of various ailments such as dry eye, congestion, rhinitis, stomatitis, gingivitis, stomach bloating, gastritis, diarrhea, constipation, cystitis, and vaginitis. It is also known that the skin is affected by the state of capillaries. A decrease in the number of capillaries leads to reduction of the metabolism and turnover of epidermal cells, as well as reduction of the number of elastic fibers due to decreased dermal fibroblast activity, etc. This can cause cosmetic problems such as spots, wrinkles, sagging, and dullness of the skin. Moreover, worsening of blood flow due to a reduced number of capillaries affects hair matrix cells causing hair problems such as dry hair, dandruff, hair loss, and graying.

Unlike arteries and veins that are composed of three layers, namely the tunica intima, the tunica media, and the tunica externa, capillaries are composed of only the tunica intima. The tunica intima of capillaries is composed of vascular endothelial cells and a basement membrane that lines the vascular endothelial cells. Arteries in the skin rise up from the subcutaneous tissue to the dermis to form a subcutaneous plexus that spreads out like a planar network in the dermis layer. Capillaries branching off from the subcutaneous plexus rise further upward to form a subpapillary plexus that spreads out like a planar network in the subpapillary layer. Capillaries branching off from the subpapillary plexus rise even further upward to form capillary loops in the papillary dermis, which is directly below the epidermal basement membrane that serves as a boundary with the epidermis, whereby oxygen and nutrients can be delivered up to epidermal cells present in the epidermal basement membrane.

Vascular endothelial cells are connected to each other mainly through the action of the cell adhesion molecule VE-cadherin and also interact with the extracellular matrix via the basement membrane through the action of integrin expressed on the cell membranes of the endothelial cells (NPL 1). Furthermore, it is known that adhesion molecules such as integrin are also expressed by fibroblasts and fibroblasts also interact with the extracellular matrix (NPL 2).

CITATION LIST

Non-Patent Literature

[NPL 1] Nat. Rev. Cancer (2008), 8(8): 604-617
[NPL 2] J. Inv. Dermatology (2013) vol. 133, 899-906

SUMMARY

Technical Problem

The purpose of the present invention is to provide a substance that has an effect of contributing to the stabilization, functional improvement, and increase of capillaries, thereby improving symptoms associated with a decrease and deterioration of capillaries.

Solution to Problem

The present inventors considered that adhesion molecules in vascular endothelial cells constituting capillaries contribute to the stabilization, increase in function, and increase in number of capillaries. Based on this idea, it was discovered that from among such adhesion molecules, the expression of VE-cadherin, which is abundant in vascular endothelial cells, and integrin α5, which contributes to adhesion between vascular cells and the cell matrix, contribute to the structure of capillaries, and thereby the present invention was achieved.

Specifically, the present invention relates to the following:

[1]
An expression promoting agent of an adhesion molecule in vascular endothelial cells comprising a yeast extract or an extract from a plant selected from the group consisting of *Calendula officinalis*, Siberian ginseng, and *Cistanche salsa*.

[2]
The expression promoting agent of an adhesion molecule according to item 1 comprising an extract from a plant selected from the group consisting of *Calendula officinalis*, Siberian ginseng, and *Cistanche salsa*.

[3]
The expression promoting agent of an adhesion molecule according to item 2, wherein the adhesion molecule is VE-cadherin.

[4]
The expression promoting agent of an adhesion molecule according to item 1 comprising a yeast extract or an extract from a plant selected from Siberian ginseng and *Cistanche salsa*.

[5]
The expression promoting agent of an adhesion molecule according to item 4, wherein the adhesion molecule is integrin α5.

Advantageous Effects of Invention

The expression promoting agent of an adhesion molecule comprising a yeast extract or an extract from a plant selected from the group consisting of *Calendula officinalis*, Siberian ginseng, and *Cistanche salsa* can promote the expression of adhesion molecules in vascular endothelial cells. By promoting the expression of such adhesion molecules, the stabilization, improvement of function, and increase in the number of capillaries can be achieved.

DESCRIPTION OF EMBODIMENTS

Figure 1:
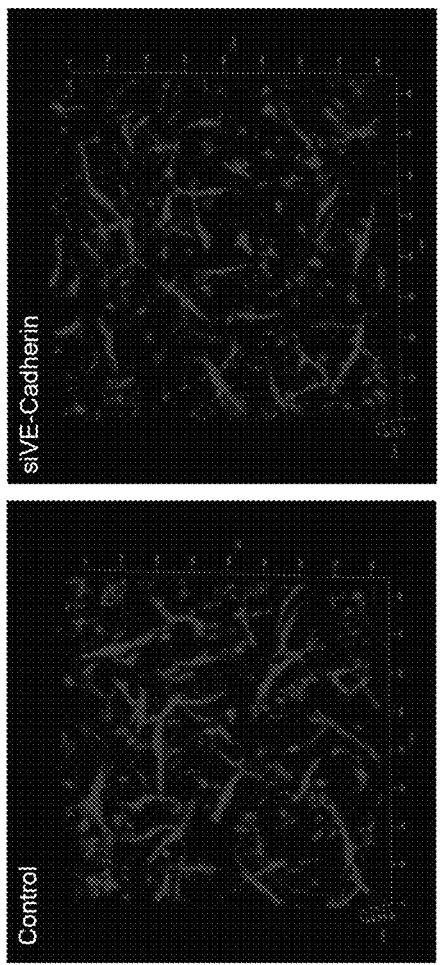
FIG. 1A is a fluorescence micrograph in which the vascular structure has been labelled in a skin model prepared by using human umbilical vein endothelial cells (HUVEC) in which gene expression of VE-cadherin has been suppressed.
FIGS. 1B to 1D are graphs showing the length (μm), volume (μm$^3$), and cross-sectional area (μm$^2$) of blood vessels measured from the fluorescent micrograph of FIG. 1A compared to a control.
Figure 1:
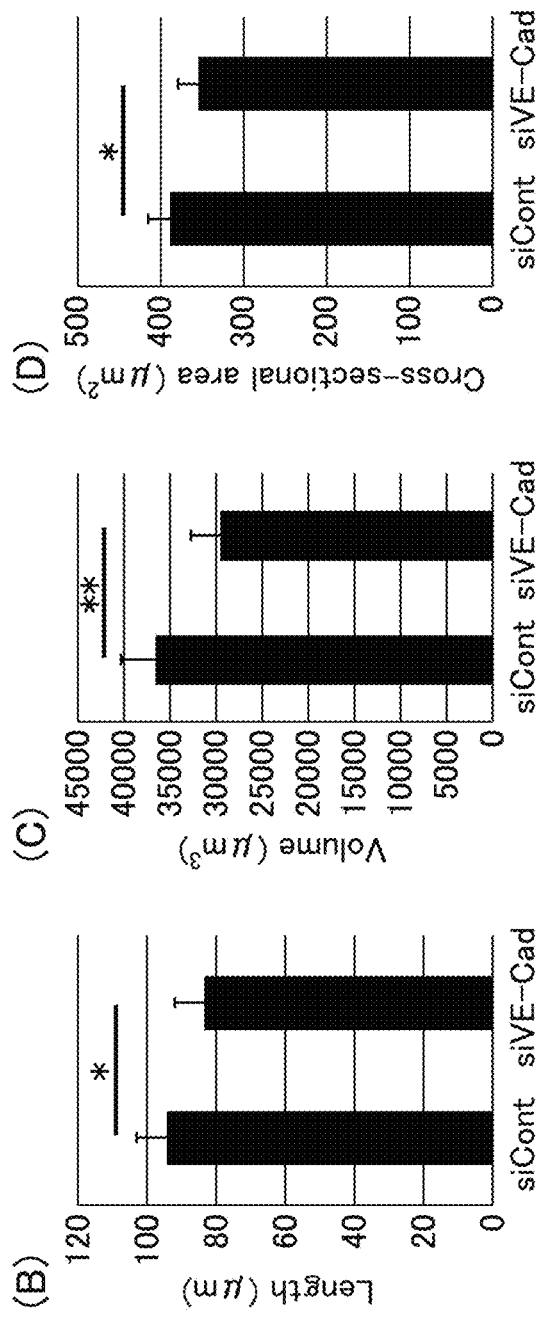

The present invention relates to an expression promoting agent of an adhesion molecule in vascular endothelial cells comprising a yeast extract or an extract from a plant selected from the group consisting of *Calendula officinalis*, Siberian ginseng, and *Cistanche salsa*. The cell adhesion molecule is preferably one that is expressed in vascular endothelial cells. Examples of such cell adhesion molecules include cadherin and integrin, specifically VE-cadherin and integrin α5.

The present invention can screen candidate drugs by a screening method in which the expression of an adhesion molecule in vascular endothelial cells is used as an indicator. The screening method comprises the following steps:
culturing vascular endothelial cells in a culture medium containing a candidate drug;
measuring the gene expression of an adhesion molecule in the vascular endothelial cells; and
determining that the candidate drug is a substance that increases the expression of the adhesion molecule if the expression increases compared to a control.

The control differs in that gene expression of the adhesion molecule is measured for vascular endothelial cells cultured in a culture medium not containing the candidate drug. Experiments with the control may be carried out in parallel to the screening method of the present invention or may be carried out beforehand.

The screening method of the present invention may include a pre-culturing step of culturing vascular endothelial cells before the step of culturing vascular endothelial cells in a culture medium containing the candidate drug. A post-culturing step of further culturing the vascular endothelial cells in a culture medium not containing the candidate drug after the step of culturing the vascular endothelial cell in a culture medium containing the candidate drug may also be included. The step of culturing vascular endothelial cells in a culture medium containing the candidate drug may be carried out by directly adding the candidate drug or a dilute solution thereof to the culture obtained in the pre-culturing step and then culturing the cells or by transferring the culture to a culture medium containing the candidate drug and then culturing the cells.

The measurement of the gene expression of adhesion molecules can be determined by measuring the amount of mRNA or protein of adhesion molecule in vascular endothelial cells. The amount of mRNA can be measured using a method known in this technical field such as quantitative PCR or northern blotting. The amount of protein can be measured using any known method in this technical field such as western blotting, immunostaining, and FACS. In these methods, antibodies that bind specifically to adhesion molecules are used.

Herein, substances that increase the expression of adhesion molecules such as VE-cadherin and/or integrin α5 in vascular endothelial cells demonstrate at least one effect selected from the group consisting of stabilization, protection, increase in number, and improvement in function of capillaries. Thus, substances that increases the expression of adhesion molecules in vascular endothelial cells can also be used as drugs for the stabilization, protection, increase in number, and improvement in function of capillaries.

Vascular endothelial cells constitute the tunica intima of blood vessels. Arteries and veins are composed of three layers, namely the tunica intima, the tunica media, and the tunica externa whereas capillaries are composed of only the tunica intima comprising vascular endothelial cells. Vascular endothelial cells are connected to each other mainly through the action of the cell adhesion molecule VE-cadherin and are connected to the extracellular matrix through the action of integrin. Vascular endothelial cells may be endothelial cells acquired from a living body, cells subcultured therefrom, cells from an established cell line, human umbilical vein endothelial cells, or cells subcultured therefrom. The vascular endothelial cells may be, but not limited to, HUVEC or HMEC-1.

VE-cadherin, also known as cadherin 5 and CD144, is a protein belonging to the cadherin super family and has a molecular weight of 140 kDa. VE-cadherin is specific to endothelial cells and is expressed in lymphatic endothelial cells and vascular endothelial cells, existing in the cell membrane. It is known that the VE-cadherin molecule is involved in the permeability of the vascular endothelium and lymphatic endothelium. It is thought that when expression of VE-cadherin increases, adhesion between vascular endothelial cells increases thereby contributing to stability of the vascular endothelium. In skin models created from vascular endothelial cells and fibroblasts, skin models using vascular endothelial cells in which VE-cadherin expression was suppressed were demonstrated to have difficulty in forming vessel-like structures (FIGS. 1 A to D). Without wishing to be bound by any theory, from common technical knowledge and from the results of these experiments, it has been shown that when the expression of VE-cadherin is suppressed the stability of capillaries is lost and the amount of capillaries is reduced.

Figure 2:
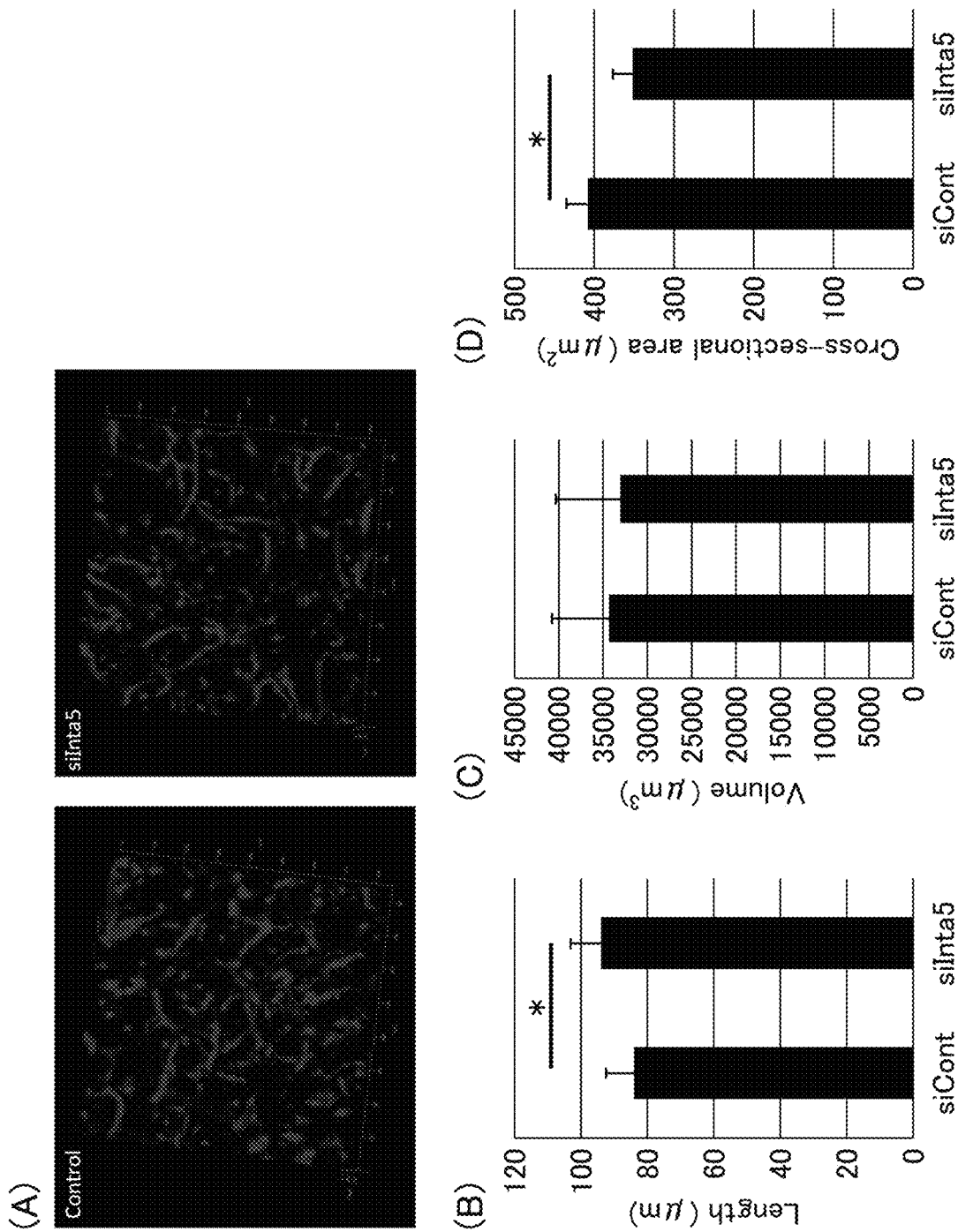
FIG. 2A is a fluorescence micrograph in which the vascular structure has been labelled in a skin model prepared by using human umbilical vein endothelial cells (HUVEC) in which gene expression of integrin α5 has been suppressed.
FIGS. 2B to 2D are graphs showing the length (μm), volume (μm$^3$), and cross-sectional area (μm$^2$) of blood vessels measured from the fluorescent micrograph of FIG. 2A compared to a control.
Figure 3:
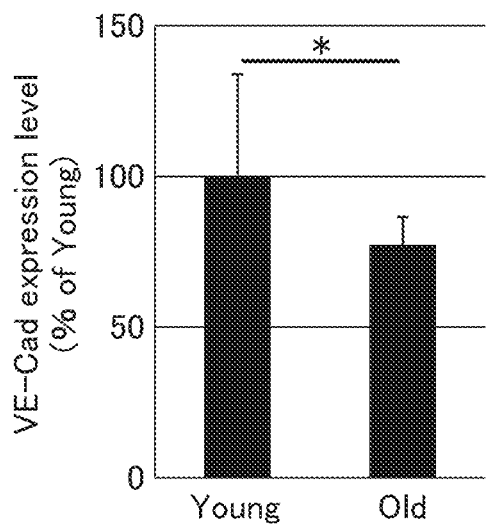
FIGS. 3A to 3D are graphs comparing the gene expression levels of VE-cadherin, integrin α3, integrin α5, and integrin α6 in vascular endothelial cells obtained from young subjects and old subjects.
Figure 3:
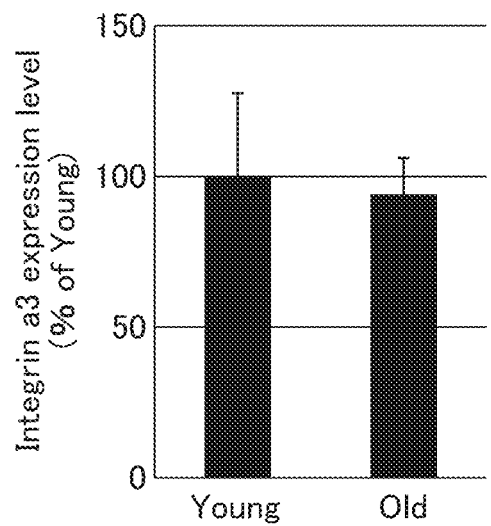
Figure 3:
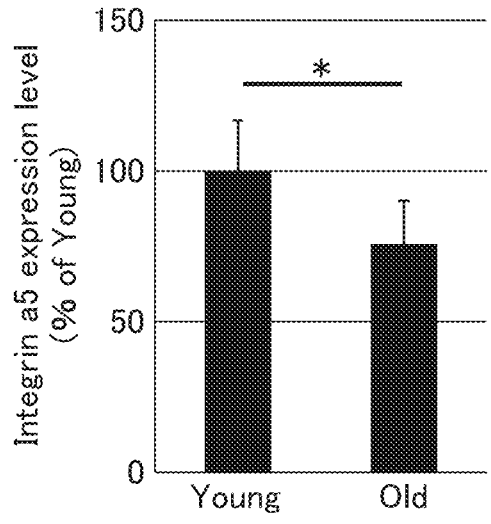
Figure 3:
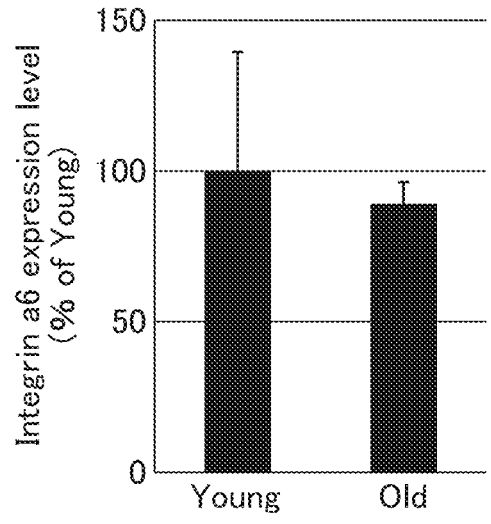

Integrin is a cell membrane protein that exists in the cell membrane and functions as a cell adhesion molecule interacting with the extracellular matrix and basement membrane. Integrin exists as a heterodimer in which α and β chains associate. At least 18 types of α subunit and 8 types of β subunit have been confirmed. Integrin α5 primarily associates with integrin β1 and is known to form integrin α5β1. Integrin α5β1 is also known as VLA-5 and a fibronectin receptor. Integrin α5 expressed in cell membranes of vascular endothelial cells bind to the fibronectin that constitutes the extracellular matrix (ECM). In skin models created from vascular endothelial cells and fibroblasts, skin models using vascular endothelial cells in which integrin α5 expression was suppressed exhibited no change in the volume of blood vessels (FIG. 2C), but a decrease in the number of intersections (FIG. 2D) and an increase in the length of the blood vessel (FIG. 2B). It is thought that since interactions with the extracellular matrix become weak, it becomes easier for the blood vessel to be extended. From among integrins expressed by endothelial cells, it has been shown that the expression of integrin α5 decreases with age (FIG. 3C), whereas there was little change in the expression levels of integrin α3 and α6 with age (FIGS. 3B and D). Without wishing to be bound by any theory, from common technical knowledge and from the results of these experiments, it has been shown that when the expression of integrin α5 is suppressed, interactions between capillaries and the extracellular matrix become weak and as a result stability of capillaries is lost.

Figure 4:
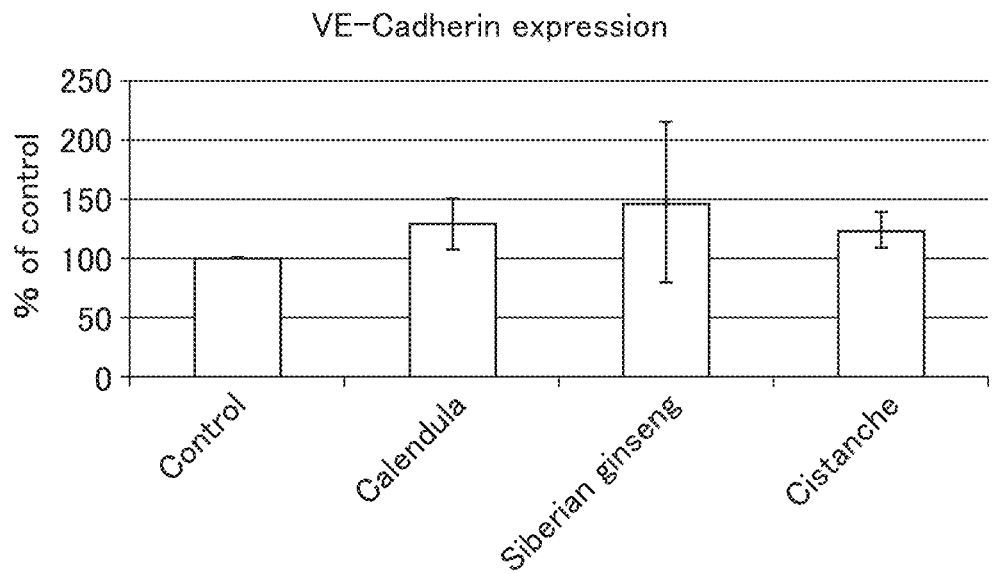
FIG. 4 is a graph illustrating the effect on VE-cadherin expression in vascular endothelial cells of extracts of Siberian ginseng, *Calendula officinalis*, and *Cistanche salsa* screened using VE-cadherin as an indicator.

A substance having an adhesion molecule expression promoting effect, which was screened in accordance with the screening method of the present invention may be considered to be a VE-cadherin gene expression promoting agent if VE-cadherin gene expression is used as an indicator. The VE-cadherin gene expression promoting agent may be any substance that can promote VE-cadherin gene expression in vascular endothelial cells. In one embodiment of the screening method of the present invention, VE-cadherin gene expression in vascular endothelial cells is used as an indicator and screening is performed using a suitable library such as for cosmetic materials, food ingredients, and pharmaceutical materials. Examples of substances determined thereby to have VE-cadherin gene expression promoting activity include an extract from at least one plant selected from the group consisting of Siberian ginseng, *Calendula officinalis*, and *Cistanche salsa* (FIG. 4).

Figure 5:
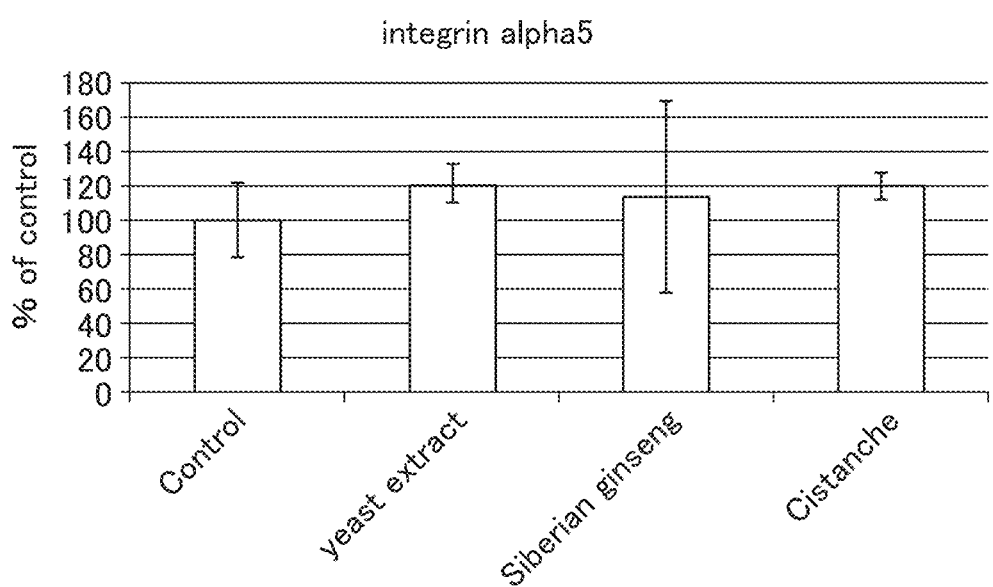
FIG. 5 is a graph illustrating the effect on integrin α5 in vascular endothelial cells of extracts of Siberian ginseng, yeast, and *Cistanche salsa* screened using integrin α5 as an indicator.

A substance having an adhesion molecule expression promoting effect, which was screened in accordance with the screening method of the present invention may be considered to be an integrin α5 gene expression promoting agent if integrin α5 gene expression is used as an indicator. The integrin α5 gene expression promoting agent may be any substance that can promote integrin α5 gene expression in vascular endothelial cells. In one embodiment of the screening method of the present invention, integrin α5 gene expression in vascular endothelial cells is used as an indicator and screening is performed using a suitable library such as for cosmetic materials, food ingredients, and pharmaceutical materials. Examples of a substance determined thereby to have integrin α5 gene expression promoting activity include yeast extract and an extract from at least one plant selected from the group consisting of Siberian ginseng, and *Cistanche salsa* (FIG. 5).

Siberian Ginseng is a plant of the family Araliaceae that is native to regions such as Russia, China, and Hokkaido and is also known as *Eleutherococcus senticosus*. Parts of the plant such as the fruit, leaf, stem, flower, and root may be used as a drug, and the root bark in particular is used as a crude drug. Siberian Ginseng extract refers to an extract from part of the Siberian Ginseng plant, specifically the root bark, which is extracted by a solvent, for example, water or an alcohol such as propylene glycol or ethanol. A Siberian Ginseng extract that is commercially available as a raw material for cosmetics or as an ingredient in health food may be used.

Calendula extract is an extract of the *Calendula officinalis* flower. *Calendula officinalis* is a plant of the family Asteraceae that is native to Southern Europe. *Calendula officinalis* extract refers to an extract from the flower of the *Calendula officinalis* which is extracted by a solvent, for example, water or an alcohol such as propylene glycol or ethanol. A *Calendula officinalis* extract that is commercially available as a raw material for cosmetics or as an ingredient in health food may be used.

Cistanche (Nikujuyou) extract is an extract of parts of the plant *Cistanche salsa*. *Cistanche salsa* is a plant of the family Orobanchaceae that is native to Central Asia from inland China. Parts of the plant such as the stem, leaf, flower, and root may be used, and specifically the dried fleshy stem is referred to as Cistanche (Nikujuyou) and is used as a crude drug. Cistanche extract refers to an extract from *Cistanche salsa* which is extracted by a solvent, for example, water or an alcohol such as propylene glycol or ethanol. A Cistanche extract that is commercially available as a raw material for cosmetics or as an ingredient in health food may be used.

The yeast extract is an extract from yeast such as *Saccharomyces cerevisiae*. The yeast extract is obtained by degrading the cell wall of the yeast by acid treatment, alkali treatment, enzymatic treatment, etc. A yeast extract that is commercially available as a raw material for cosmetics or as an ingredient in health food may be used.

The aforementioned plant and yeast extracts may be obtained by conventional methods. For example, the plants or the yeast which is the source of the extract may be immersed in an extraction solvent at room temperature or heated, or heated under reflux, then filtered, and concentrated to obtain the extract. The extraction solvent may be any solvent that is normally used for extraction. For example, aqueous solvents such as water, physiological saline, phosphate buffer, borate buffer, and organic solvents, alcohols such as ethanol, propylene glycol, 1,3-butylene glycol, and glycerin, and hydrous alcohols, chloroform, dichloroethane, carbon tetrachloride, acetone, ethyl acetate, and hexane may be used individually or in combination. Preferably, water is used as the solvent. The extract obtained by extraction using any of the aforementioned solvents may be used as is, or an extract that has been concentrated by, for example, lyophilization may be used. Furthermore, if necessary, an extract from which impurities have been removed by an adsorption method such as the use of an ion exchange resin, or an extract that has been further concentrated by adsorption on a porous polymer column (e.g. amberlite XAD-2) followed by elution with a desired solvent may also be used.

Substances that have adhesion molecule expression promoting effects in vascular endothelial cells selected from the screening methods of the present invention can also be referred to as agents for protecting, improving, increasing the number of, and improving the function of capillaries. These substances may be incorporated into cosmetics, pharmaceuticals, and quasi drugs and may also be incorporated into foods and dietary supplements such as nutritional supplements. Substances that have adhesion molecule expression promoting effects of the present invention, namely VE-cadherin gene expression promoting agents or integrin α5 gene expression promoting agents, and agents for protecting, improving, increasing the number of, and improving the function of capillaries may be administered via any route but in order to act on vascular endothelial cells, administrative routes such as oral, transdermal, or transmucosal administration are preferred.

As described above, the promotion of VE-cadherin gene expression and/or integrin α5 gene expression in vascular endothelial cells was found to contribute to the protection, improvement, increase in number, and increase in function of capillaries. Thus, another embodiment of the present invention relates to an agent for the protection, improvement, increase in number, and increase in function of capillaries comprising a VE-cadherin gene expression agent and/or integrin α5 gene expression agent, and more specifically also relates to a method for protecting, improving, increasing the number of, and increasing the function of capillaries comprising the application of an expression promoting agent of adhesion molecules in vascular endothelial cells. The adhesion molecules in the vascular endothelial cells pertaining thereto are VE-cadherin and/or integrin α5. Yet another embodiment relates to a method for protecting, improving, increasing the number of, and increasing the function of capillaries comprising the application on the skin of a VE-cadherin gene expression promoting agent and/or an integrin α5 gene expression promoting agent. Furthermore, the extracts specified in the present invention can be used and function to improve swelling, dullness, atopic dermatitis, rosacea, dry eye, xerostomia, coldness, rough skin, hair loss, etc. by protecting, improving, increasing the number of, and increasing the function of capillaries.

Herein, the method for protecting, improving, increasing the number of, and increasing the function of capillaries relates to a beautification method for the purpose of beautification and can be differentiated from a medical treatment performed by a physician or by medical personnel. Such a beautification method may be performed on oneself, or may be performed at hair salons, cosmetics stores, or beauty salons.

All documents mentioned herein are incorporated herein by reference in their entirety.

The examples of the present invention described below are for illustrative purposes only and do not limit the technical scope of the present invention. The technical scope of the present invention is limited only by the claims. Modifications of the present invention, for example, additions, deletions and replacements of the constituent features can be made without departing from the spirit of the present invention.

EXAMPLES

Example 1: Creation of Skin Model

Three wells of a six-well plate were used to create a skin model by the following method. A collagen gel was prepared by adding 16.7 ml of 0.3% collagen to a 50 ml tube on ice and slowly adding 10.6 ml of DMEM(−) culture medium while stirring. Next, human fibroblasts (HF) were prepared in the DMEM(−) culture medium so as to reach a density of $10 \times 10^5$ cells/ml. Human umbilical vein endothelial cells (HUVEC) were prepared in a 0.5% FBS-supplemented EBM2 culture medium so as to reach a density of $10 \times 10^5$ cells/ml. For the HF group, 2 ml of prepared HF culture was taken, and for the HF-HUVEC group 2 ml of each of the prepared HF culture and HUVEC culture were taken. This was mixed with 6 ml of 0.5% FBS-supplemented EBM2 culture medium to prepare 10 ml of cell solution. The prepared 10 ml of cell solution was stirred over ice with 10 ml of collagen gel solution and then poured into the 6-well plate with 6 ml to one well. The well plate was shaken overnight in a 5% moist atmosphere at 37° C., then left standing for 5 days at 37° C. to create an HF skin model and an HF-HUVEC skin model. In the HF-HUVEC skin model, HUVEC cells were observed to take the form of blood vessels.

Example 2: Suppression of Gene Expression of Vascular Endothelial Cells

In HUVEC cells, siRNAs (Ambion Silencer Select siRNAs: CDH5 (ID: s2780, s2781, s2782), ITGA3 (ID: s7541, s7542, s7543), ITGA5 (ID: s7547, s7548.s7549), ITGA6 (ID: s7492, s7493, s7494)) were used to suppress gene expression of VE-cadherin (cad), integrin α3 (inta3), integrin α5 (inta5), and integrin α6 (inta6). HUVEC cells were prepared so as to reach a density of $10 \times 10^5$ cells/ml. The cells were sedimented and the culture medium aspirated, then 100 μl of a solution from a kit was added and mixing was performed. 1 μl of each of the aforementioned siRNAs (Ambion) were added to the cell mixtures and the whole amount was transferred to a 4D-Nucleofecter (Lonza) cuvette. The cell type was set to HUVEC, the 4D-Nucleofecter was started and gene transfer was performed. 500 μl of EBM2(+) culture medium was added to each cuvette after gene transfer and the entire contents of the cuvette was added to a 10 cm petri dish in which 10 ml of EBM2(+) culture medium had been added beforehand. The petri dish was left standing overnight at 37° C. and the next day the cells were used to create a skin model in the same way as described in EXAMPLE 2. For each of the cells transfected with siRNA, quantitative PCR was carried out and suppression of expression of the target gene was confirmed (data not provided).

In the skin models for which siRNAs were transfected and gene expression of VE-cadherin, integrin α3, integrin α5, and integrin α6 had been suppressed, anti-CD31 antibodies (R&D systems) were used as primary antibodies and Alexa Fluor 488 labelled anti-sheep antibodies (Invitrogen) were used as secondary antibodies so that the vascular endothelial cells could be visualized (FIGS. 1A and 2A). In a skin model in which expression of VE-cadherin and integrin α5 had been suppressed, changes to the structure of the blood vessels were observed. Using image analysis software (Imaris), the length (μm), volume (μm$^3$), and cross-sectional area (μm$^2$) of the blood vessels were measured and for cases in which VE-cadherin expression had been suppressed, there was a significant reduction in all these dimensions compared to the control (FIGS. 1B to D) (*: p<0.05, **: p<0.01). For cases in which integrin α5 expression was suppressed, there was a significant reduction in the length (μm) and cross-sectional area (μm$^2$) of the blood vessels compared to the control (FIGS. 2B to D) (*: p<0.05).

Example 3: Effects on Aging in Skin Model

Vascular endothelial cells from young subjects (aged 0) and old subjects (aged 50) were inoculated onto a 6-well plate at a cell density of $2 \times 10^5$ cells/well and left standing overnight. The following day, RNA was extracted therefrom using RNeasy mini kit (QIAGEN). The concentration of the extracted RNA was measured using NanoDrop, and RNase-free water was used to prepare 100 ng/ml thereof. TaqMan RNA-to-C 1-Step Kit (Applied Biosystems) was used to quantify the prepared RNA by real-time PCR (Roche Lightcycler 480II) using primers for the following genes. Using β-actin (b-actin: Cat #Hs01060665_g1) as an internal standard, a significant difference in expression levels was observed with respect to VE-cadherin (VE-Cadherin: Cat #Hs00170986_m1) and integrin α5 (Integrin alpha5: Cat #Hs01547673_m1) between cells derived from young subjects and cells derived from old subjects (FIGS. 3A to D: *: P<0.05), whereas with respect to integrin α3 (Integrin alpha3: Cat #Hs01076879_m1) and integrin α6 (Integrin alpha6: Cat #Hs01041011_m1) a significant difference in expression levels was not observed.

Example 4: Screening Method of Substances Having VE-Cadherin Expression Promoting Effect Using VE-Cadherin Gene Expression as an Indicator Human umbilical vein endothelial cells (HUVEC) were prepared in a 0.5% FBS-supplemented EBM2 culture medium so to reach a cell density of $10\times10^5$ cells/ml and cultured in a moist 5% $CO_2$ atmosphere at 37° C. A cosmetic materials library was used for the candidate drugs. The candidate drugs were added and culturing was performed for 6 hours. After culturing, the culture medium was removed, and RNA was extracted from the cells using RNeasy mini kit (QIAGEN). The concentration of the extracted RNA was measured by NanoDrop, and RNase-free water was used to prepare 100 ng/ml thereof. TaqMan RNA-to-C 1-Step Kit (Applied Biosystems) was used to quantify the prepared RNA by real-time PCR (Roche Lightcycler 480II) using primers for the VE-cadherin gene.

When extracts of Siberian ginseng, *Calendula officinalis*, and *Cistanche salsa* were used as the candidate drugs, expression of the VE-cadherin gene significantly increased compared to the control ($p<0.05$: FIG. 4). These extracts were selected as substances having VE-cadherin expression promoting activity.

Example 5: Screening Method of Substances Having Integrin α5 Expression Promoting Effect Using Integrin α5 Gene Expression as an Indicator Human umbilical vein endothelial cells (HUVEC) were prepared in a 0.5% FBS-supplemented EBM2 culture medium so as to reach a density of $10\times10^5$ cells/ml and were cultured in a moist 5% $CO_2$ atmosphere at 37° C. The candidate drugs were added and culturing was performed for 6 hours. After culturing, the culture medium was removed, and RNA was extracted from the cells using RNeasy mini kit (QIAGEN). The concentration of the extracted RNA was measured by NanoDrop, and RNase-free water was used to prepare 100 ng/ml thereof. TaqMan RNA-to-C 1-Step Kit (Applied Biosystems) was used to quantify the prepared RNA by real-time PCR (Roche Lightcycler 480II) using primers for the integrin α5 gene.

When Siberian ginseng, yeast and Cistanche extracts were used as the candidate drugs, the expression of the integrin α5 gene increased significantly compared to the control ($p<0.05$: FIG. 5). These extracts were selected as substances having firmness improving activity.

The invention claimed is:

1. A method for stabilizing capillaries, or increasing the function or number of capillaries in a subject who suffers from decreased capillaries, through promoting an expression promoting agent of an adhesion molecule in vascular endothelial cells comprising administering a yeast extract to the subject.

2. The method of claim 1, wherein the adhesion molecule is integrin α5.

3. The method of claim 1, wherein the administering comprises applying the yeast extract to the skin of the subject.

4. The method of claim 1, wherein the subject is suffering from swelling, dullness, atopic dermatitis, rosacea, dry eye, xerostomia, coldness, rough skin, or hair loss.

* * * * *